US006455680B1

(12) United States Patent
Lukin

(10) Patent No.: US 6,455,680 B1
(45) Date of Patent: Sep. 24, 2002

(54) METHODS UTILIZING ARYL THIOIMINES IN SYNTHESIS OF ERYTHROMYCIN DERIVATIVES

(75) Inventor: Kirill A. Lukin, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 125 days.

(21) Appl. No.: 09/747,724

(22) Filed: Dec. 21, 2000

(51) Int. Cl.[7] ............................................. C07H 17/08
(52) U.S. Cl. ........................... 536/7.3; 536/7.2; 536/7.4
(58) Field of Search ............................ 536/7.2, 7.3, 7.4

(56) References Cited

U.S. PATENT DOCUMENTS

| 4,331,803 A | 5/1982 | Watanabe et al. ............. 536/7.2 |
| 4,496,717 A | * 1/1985 | Adachi et al. ................ 536/7.2 |
| 5,274,085 A | 12/1993 | Amano et al. ................ 536/7.4 |
| 5,866,549 A | 2/1999 | Or et al. ........................ 514/29 |
| 5,872,229 A | 2/1999 | Liu et al. ..................... 536/18.6 |
| 5,919,916 A | 7/1999 | Gracey et al. ................ 536/7.2 |
| 5,932,710 A | 8/1999 | Liu et al. ..................... 536/18.7 |
| 6,040,440 A | 3/2000 | Graham et al. ............. 536/124 |
| 6,075,011 A | 6/2000 | Or et al. ........................ 514/29 |
| 6,124,269 A | 9/2000 | Phan et al. .................... 514/29 |

OTHER PUBLICATIONS

Greene and Wuts, Protective Groups in Organic Synthesis, 2nd Edition, John Wiley & Sons, Inc., 1991.

* cited by examiner

*Primary Examiner*—Dwayne C. Jones
(74) *Attorney, Agent, or Firm*—B. Gregory Donner

(57) ABSTRACT

An efficient deoximation technique for use in synthesis of erythromycin derivatives, involving aryl thioimine intermediates is disclosed. The aryl thioimine intermediates can be utilized in a method for protecting a ketone of a ketone-containing erythromycin derivative as a thioimine; a method for deoximating an oxime-containing erythromycin derivative, or a method for preparing a 6-O-alkyl erythromycin derivative. Presently preferred erythromycin derivatives have a C-9 oxime or a C-9 ketone.

28 Claims, No Drawings

METHODS UTILIZING ARYL THIOIMINES IN SYNTHESIS OF ERYTHROMYCIN DERIVATIVES

FIELD OF THE INVENTION

The present invention is directed to an efficient deoximation technique for use in the synthesis of erythromycin derivatives, involving aryl thioimine intermediates. The aryl thioimine intermediates can be utilized in a method for protecting a ketone of a ketone-containing erythromycin derivative as a thioimine; a method for deoximating an oxime-containing erythromycin derivative, or a method for preparing a 6-O-alkyl erythromycin derivative. Presently preferred erythromycin derivatives have a C-9 oxime or a C-9 ketone.

BACKGROUND OF THE INVENTION

Erythromycins A through D, represented by Formula I and Table 1 shown below, are well-known and potent anti-bacterial agents, used widely to treat and prevent bacterial infection.

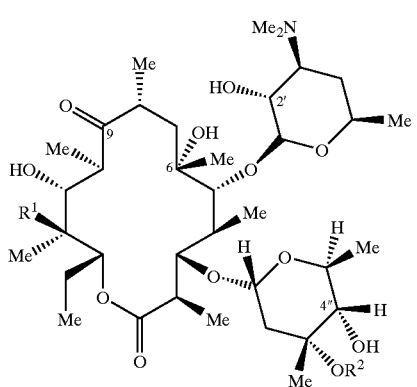

Formula I

TABLE 1

| Erythromycin | $R^1$ | $R^2$ |
|---|---|---|
| A | —OH | —Me |
| B | —H | —Me |
| C | —OH | —H |
| D | —H | —H |

As with other anti-bacterial agents, however, bacterial strains having resistance or insufficient susceptibility to erythromycin have been identified. Also, erythromycin A has only weak activity against Gram-negative bacteria. Therefore, there is a continuing need to identify and synthesize new erythromycin derivative compounds which possess improved anti-bacterial activity, which have lower potential for developed resistance, which possess the desired Gram-negative activity, or which possess unexpected selectivity against target microorganisms.

Generally, 6-O-alkyl derivatives of erythromycin are known as anti-bacterial agents. 6-O-methyl erythromycin A (clarithromycin A, disclosed in U.S. Pat. No. 4,331,803) and 6-O-methyl erythromycin B (clarithromycin B, disclosed in U.S. Pat. No. 4,496,717) are potent macrolide antibiotics.

More recently, 6-O-substituted derivatives of erythromycin having improved antibacterial activity have been disclosed in U.S. Pat. Nos. 5,866,549; 5,872,229; 5,919,916; 5,932,710; 6,040,440; 6,075,011 and 6,124,269 among others.

Synthetic techniques for 6-O-substituted erythromycin derivatives generally involve protection of a C-9 ketone as an oxime, followed by protection of the 2'- and 4"-hydroxyl groups prior to 6-O-alkylation. Subsequent to 6-O-alkylation, the protecting groups are removed.

The deoximation reaction has been carried out according to methods described by Greene and Wuts in *Protective Groups in Organic Synthesis*, 2nd Ed., John Wiley & Son, Inc, 1991, and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate and potassium metabisulfite among others. Deoximation may also be accomplished by treatment with an inorganic nitrite salt, for example, sodium nitrite or potassium nitrite, in the presence of acid. Examples of the solvents used are protic solvents such as water, methanol, ethanol, propanol, isopropanol, trimethylsilanol or a mixture of one or more of the above solvents. The deoximation reaction has been carried out in the presence of an organic acid such as formic acid, acetic acid or trifluoroacetic acid, but may be accomplished with hydrochloric acid also.

However, the conventional techniques described above have certain disadvantages. For example, in a typical deoximation with an erythromycin oxime with sodium bisulfite, approximately 30–40% of the product may be lost as a result of decomposition, due to the relatively harsh reaction conditions. Therefore, milder methods for more efficient deoximation would be advantageous; and such a method for a more efficient deoximation could be advantageously utilized in a method for ketone protection in ketone-containing erythromycin derivatives, or in a method for making 6-O-alkyl substituted erythromycin derivatives.

BRIEF SUMMARY OF THE INVENTION

The invention is directed to a method for protecting a ketone of a ketone-containing erythromycin derivative as a thioimine comprising the steps of:

reacting a ketone of a ketone-containing erythromycin derivative with a hydroxamating agent to form an oxime; and then, reacting said oxime with a trialkyl phosphine and an aryl disulfide to form an aryl thioimine.

In the method, the ketone may be a C-9 ketone, and the aryl thioimine may be a C-9 aryl thioimine. The method may also include deprotecting the aryl thioimine in aqueous acidic solution to form a ketone-containing erythromycin derivative. The C-9 ketone containing-erythromycin derivative may have a hydroxyl group at C-6. Furthermore, the C-9 ketone is protected to alkylate C-6 with an alkylating agent. A presently preferred ketone-containing erythromycin derivative is erythromycin A and a presently preferred aryl thioimine is 9-phenylthioimino erythromycin. Moreover, the arylthioimine can be hydrolyzed to an imine with a hydrolyzing agent.

The invention is also directed to a method for deoximating a 6-O-substituted oxime-containing erythromycin derivative comprising the steps of:

reacting an oxime of a 6-O-substituted oxime-containing erythromycin derivative with a trialkyl phosphine and an aryl disulfide to form an aryl thioimine; and then, hydrolyzing said aryl thioimine in aqueous acidic solution to form a ketone-containing 6-O-substituted erythromycin derivative.

The 6-O-substituted oxime-containing erythromycin derivative may be a C-9 oxime-containing, 2'-hydroxyl-containing, 4"-hydroxyl-containing, C-6-hydroxyl-containing erythromycin derivative. For the practice of this method, the 2'-hydroxyl and 4"-hydroxyl of the C-9 oxime-containing, 2'-hydroxyl-containing, 4"-hydroxyl-containing, C-6-hydroxyl-containing erythromycin derivative can be protected with at least one hydroxyl-protecting agent to form a 2'- and 4"-hydroxyl protected aryl thioimine after aryl thioimine formation. Moreover, after such protection the 2'- and 4"-hydroxyl protected aryl thioimine can be alkylated with an alkylating agent to form a 2'- and 4"-hydroxyl protected, C-6-O-alkylated aryl thioimine. A presently preferred 2'- and 4"-hydroxyl protected, C-6-O-alkylated aryl thioimine is 9-phenylthioimino-6-O-propenylquinolinylerythromycin-2',4"-dibenzoate, and a presently preferred ketone-containing 6-O-substituted erythromycin derivative is 6-O-propenylquinolinylerythromycin-2',4"-dibenzoate.

The invention is also directed to a method of preparing a 6-O-alkyl derivative of a C-9 ketone-containing, C-6 hydroxyl-containing, 2'-hydroxyl-containing, 4"-hydroxyl-containing erythromycin derivative comprising the steps of:

reacting the C-9 ketone of a C-9 ketone-containing, C-6 hydroxyl-containing, 2'-hydroxyl-containing, 4"-hydroxyl-containing erythromycin derivative with a hydroxamating agent to form a C-9 oxime;

derivatizing said C-9 oxime with a trialkyl phosphine and an aryl disulfide to form a C-9 aryl thioimine;

protecting said 2'-hydroxyl and said 4"-hydroxyl of said C-9 aryl thioimine with at least one hydroxyl-protecting agent to form a 2' and 4"-hydroxyl protected C-9 aryl thioimine;

alkylating said C-6-hydroxyl of said 2' and 4"-hydroxyl protected C-9 aryl thioimine with an alkylating agent to form a C-6-O-alkylated 2' and 4"-hydroxyl protected C-9 aryl thioimine;

deoximating said 2' and 4"-hydroxyl protected C-6-O-alkylated C-9 aryl thioimine in aqueous acidic solution to form a 2' and 4"-hydroxyl protected C-6-O-alkylated C-9 keto-erythromycin derivative; and then isolating the desired product.

For the practice of this method, the 2' and 4"-hydroxyl protected C-6-O-alkylated C-9 keto-erythromycin derivative can be deprotected to form a 2' and 4"-hydroxyl, C-6-O-alkylated C-9 keto-erythromycin derivative. A presently preferred 2' and 4"-hydroxyl protected C-6-O-alkylated C-9 keto-erythromycin derivative is 6-O-propenylquinolinylerythromycin-2',4"-dibenzoate.

For the practice of any of the methods of the present invention, the trialkyl phosphine may be tributyl phosphine, the aryl disulfide may be diphenyl disulfide; the hydroxamating agent may be hydroxylamine, the hydroxyl-protecting agent may be benzoic anhydride, and the alkylating agent may be an alkenyl alkylating agent. A presently preferred alkenyl alkylating agent is propenyl quinoline t-butyl carbonate and a palladium catalyst.

The invention is also directed to a method for protecting the ketone of erythromycin A as a thioimine comprising the steps of:

reacting the ketone of erythromycin A with hydroxylamine to form an oxime; and then, reacting said oxime with tributyl phosphine and phenyl disulfide to form 9-phenylthioiminoerythromycin.

The invention is also directed to a method of preparing 6-O-propenylquinolinylerythromycin-2',4"-dibenzoate comprising the steps of:

reacting the C-9 ketone of erythromycin A with hydroxylamine to form erythromycin oxime;

derivatizing said oxime with tributyl phosphine and phenyl disulfide to form 9-phenylthioimino erythromycin;

protecting the 2'-hydroxyl and the 4"-hydroxyl of 9-phenylthioimino erythromycin with benzoic anhydride to form 9-phenylthioimino erythromycin 2',4"-dibenzoate;

alkylating the C-6-hydroxyl of 9-phenylthioimino erythromycin 2',4"-dibenzoate with propenyl quinoline t-butyl carbonate and a palladium catalyst to form 6-O-propenylquinolinyl-9-phenylthioimino erythromycin 2',4"-dibenzoate;

converting 6-O-propenylquinolinyl-9-phenylthioimino erythromycin 2',4"-dibenzoate in aqueous HCl into 6-O-propenylquinolinyl erythromycin 2',4"-dibenzoate; and then, isolating the desired product.

DETAILED DESCRIPTION OF THE INVENTION

Definitions of Terms

The term "alkyl" as used herein, alone or in combination, refers to $C_1$–$C_{12}$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E-and Z-pentenyl, decenyl and the like.

The term "lower" modifying "alkyl", "alkenyl", "alkynyl" or "alkoxy" refers to a $C_1$–$C_6$ unit for a particular functionality. For example lower alkyl means $C_1$–$C_6$ alkyl.

The term "alkoxyl" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted.

The term "halogen" as used herein refers to I, Br, Cl or F.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "hydroxy" as used herein, refers to —OH.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O) O—. Rings may be substituted multiple times.

The terms "erythromycin derivative" or "erythromycin derivatives" refer to erythromycins A–D (shown in Formula I and Table I) and derivatives thereof. Derivatives include substitutions for the C-2–C-13 hydrogen, hydroxy, alkyl or alkoxyl substituents of erythromycins A–D, with different hydrogen, hydroxy, alkyl or alkoxyl substituents. Other examples of useful erythromycin derivatives are disclosed in U.S. Pat. Nos. 5,866,549; 5,872,229; 5,919,916; 5,932,710; 6,040,440; 6,075,011 and 6,124,269, the disclosures of which are hereby incorporated by reference.

Abbreviations

Abbreviations which have been used in the schemes and the examples which follow are: THF for tetrahydrofuran; HPLC for high pressure liquid chromatography; IPA for isopropyl alcohol; Bz for benzoyl; Me for methyl; conc. for concentrated; dba for dibenzylidene acetone; IPAC for isopropyl acetate; PQC for propenyl quinoline t-butyl carbonate; DMAP for 4-N,N-dimethylaminopyridine; DPPB for 1,4-bis(diphenylphosphino)butane and MTBE for methyl-tert-butyl ether.

Aspects of the methods of the present are presented in the following Schemes. Scheme 1 shows a high yielding deoximation of a 6-O-alkylated erythromycin derivative, according to a method of the present invention.

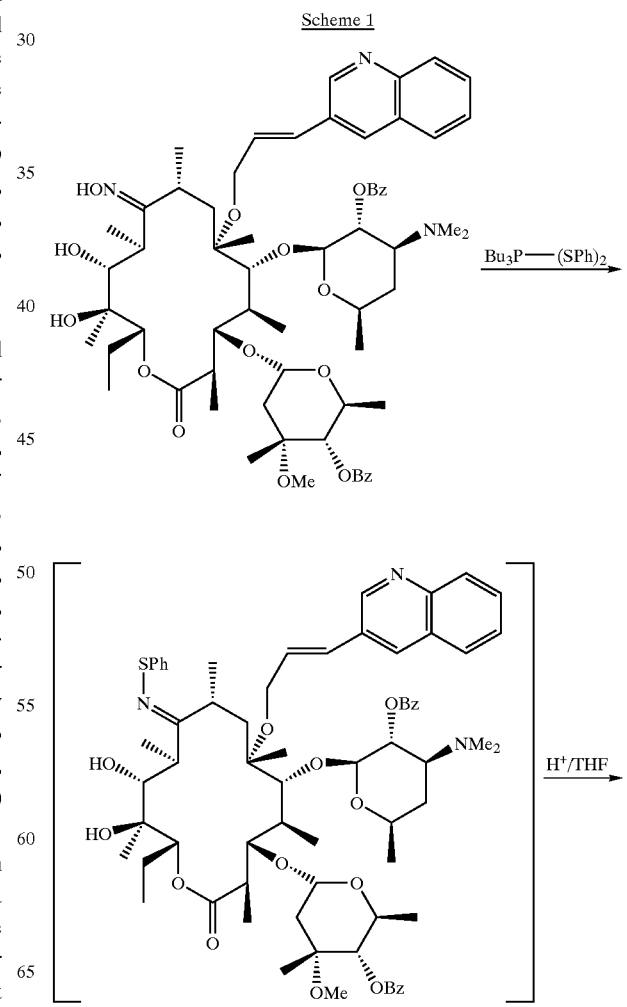

Scheme 1

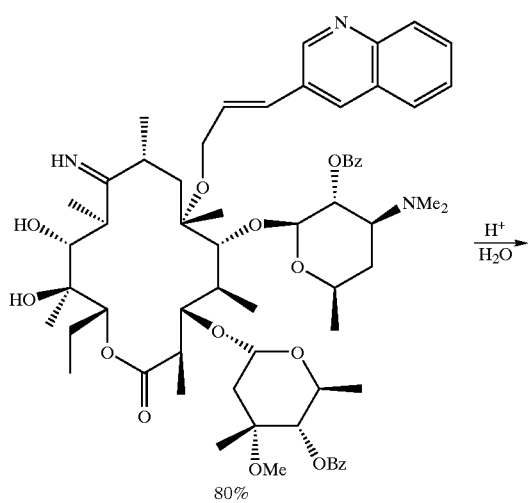
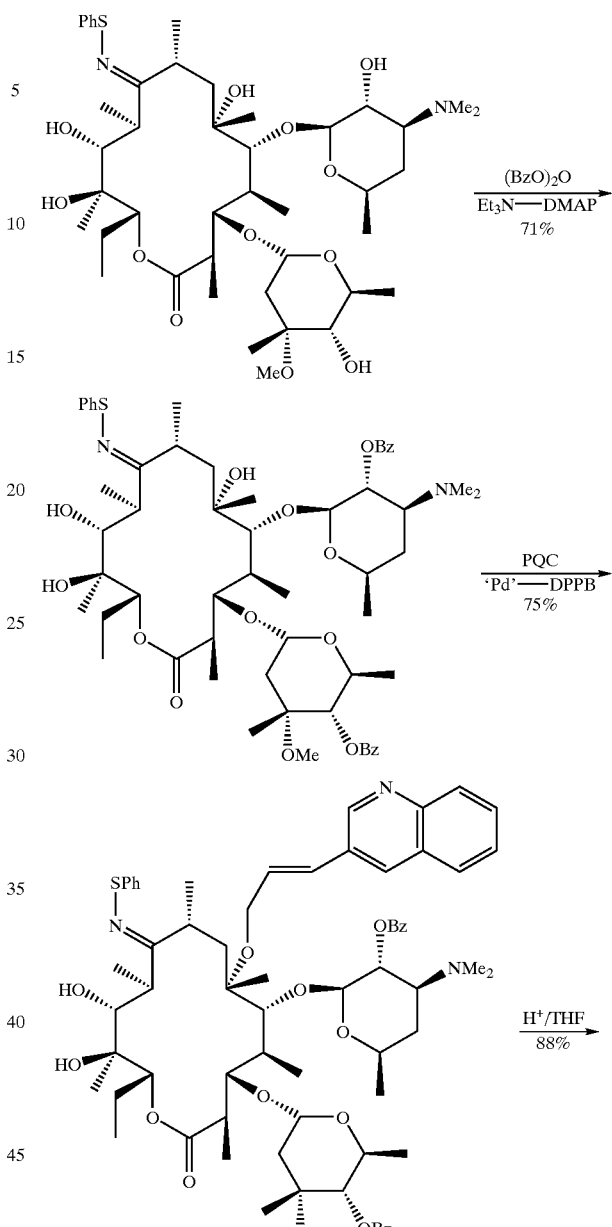
Scheme 2, shown below, illustrates a deoximation after hydroxyl group protection and C-6 alkylation, according to a method of the present invention.
Scheme 2
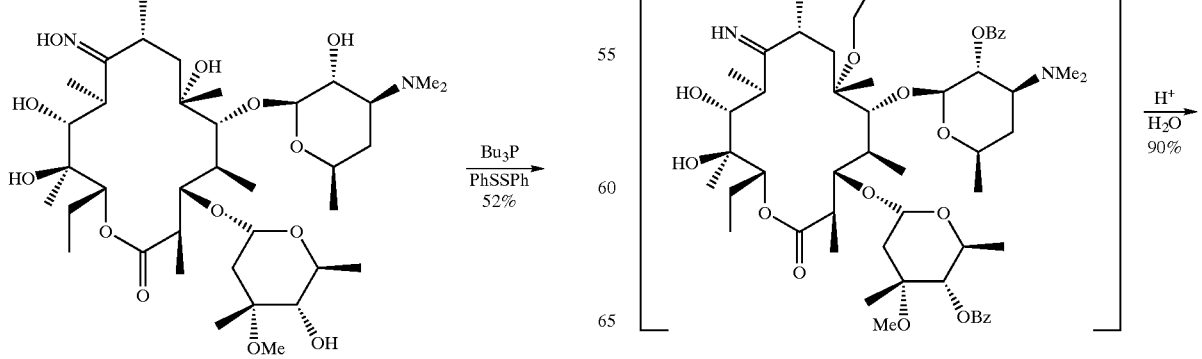

9
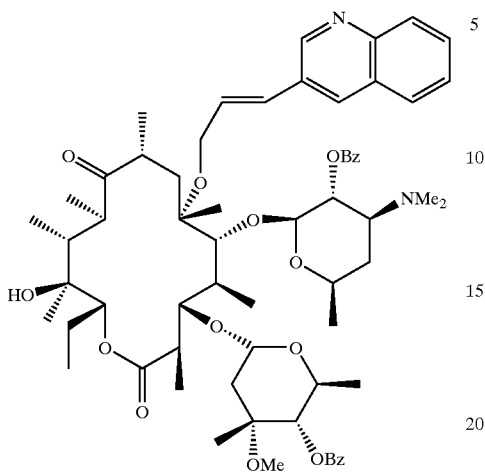
Scheme 3, shown below, illustrates the procedure of Example 1, a transformation of an oxime to a thioimine.
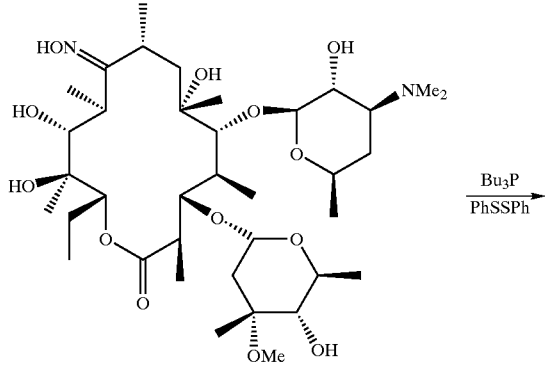
10
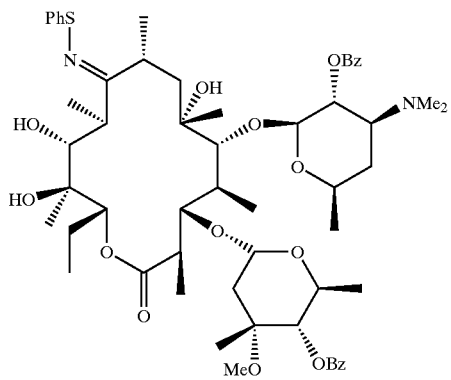
Scheme 4, shown below, illustrates the procedure of Example 3, a deoximation to a ketone.
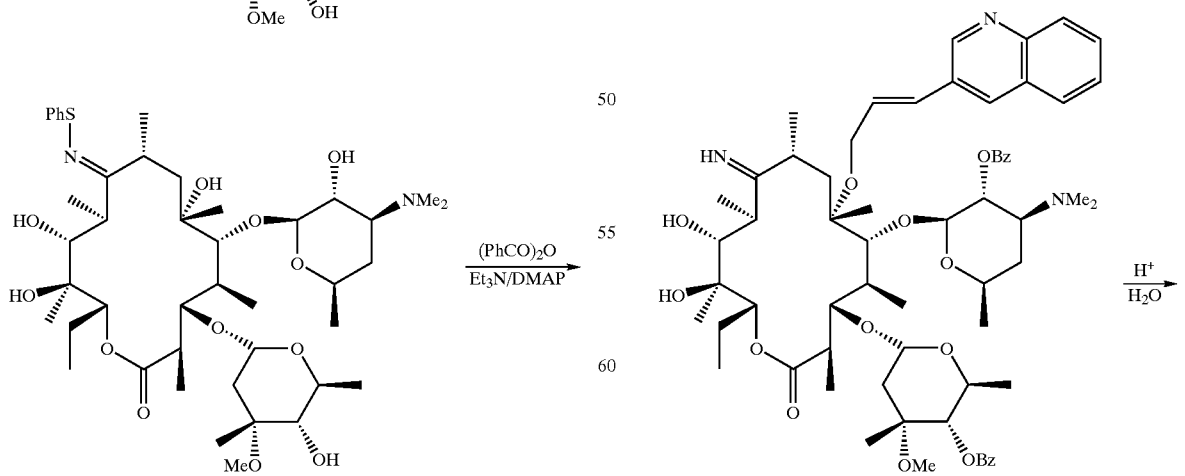

Scheme 5, shown below, illustrates the procedure of Example 5, a transformation of a thioimine to an imine.

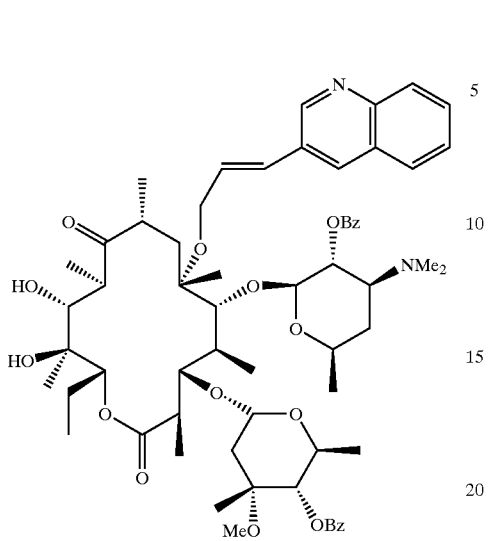

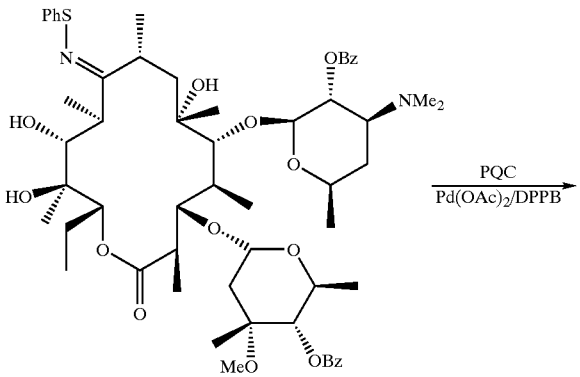

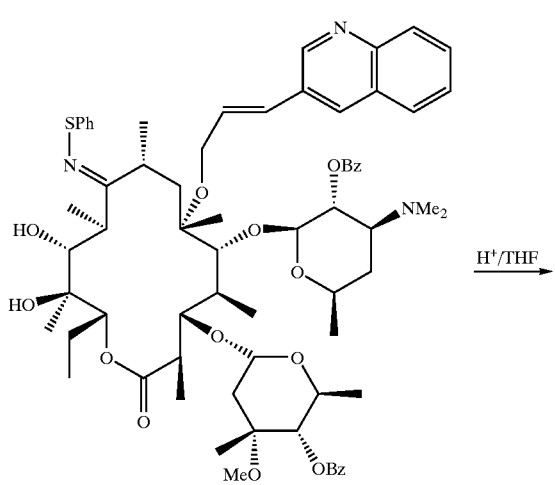

A detailed description of representative methods of the present invention is set forth in the Examples. A discussion of the various steps (hydroxyl protection/deprotection, 6-O-alkylation, hydroxamation, and formation/hydrolysis of aryl thioimines) which may be utilized in the methods of the present invention follows.

2' and 4"-Hydroxyl Protection/Deprotection

The 2' and 4"-hydroxyl groups of the erythromycin derivatives may be protected by reaction with a suitable hydroxyl protecting reagent in an aprotic solvent. Typical hydroxyl-protecting groups include, but are not limited to, acetylating agents, silylating agents and acid anhydrides, among others. For example, acetic anhydride, benzoic anhydride, benzyl chloroformate, or a trialkyl silyl chloride are among the suitable hydroxyl protecting reagents.

Examples of aprotic solvents are dichloromethane, chloroform, N,N-dimethylformamide, tetrahydrofuran, N-methylpyrrolidinone, and dimethylsulfoxide, N,N-dimethylacetamide, hexamethyl phosphoric triamide, a mixture thereof, or a mixture of one of the above solvents with ether, 1,2-dimethoxyethane, tetrahydrofuran, acetonitrile, ethyl acetate and acetone among others.

Protection of 2'- and 4"-hydroxyl groups of erythromycin derivatives may be accomplished sequentially or simultaneously, with the same or two different reagents. A particularly preferred group for protecting the hydroxyl groups is the benzoate protecting group. Benzoylation of the hydroxyl group is typically accomplished by treating the erythromycin derivative with a benzoylating agent, such as benzoyl halide or benzoyl anhydride.

The deprotection of the 2'- and 4"-hydroxyl groups is carried out in accordance with methods described in the literature, for example as described in detail in *Protective Groups in Organic Synthesis,* by T. Greene and P. Wuts, published by John Wiley & Sons in New York in 1991. When the protecting group is an ester such as acetate or benzoate, the compound may be deprotected by treatment with ethanol or methanol. When the group to be removed is a trialkylsilyl group, the compound may be deprotected by treatment with a source of fluoride in tetrahydrofuran or acetonitrile.

"Hydroxy protecting group" as used herein, refers to an easily removable group known in the art to protect a hydroxyl group against undesirable reaction during synthetic procedures, which can then be selectively removed. The use of hydroxy protecting groups is well known in the art, and is described in detail in *Protective Groups in Organic Synthesis,* by T. Greene and P. Wuts, published by John Wiley & Sons in New York in 1991. Examples of hydroxy protecting groups include, but are not limited to, methylthiomethyl, tert-dimethylsilyl and tert-butyldiphenylsilyl among others.

The term "protected hydroxy" refers to a hydroxy group protected with a hydroxy protecting group, as defined above, such as benzoyl, acetyl, trimethylsilyl, triethylsilyl or methoxymethyl groups, among others.

C-6-O-Alkylation

The alkylation of a C-6-hydroxyl containing erythromycin derivative can be carried out with an alkylating agent in a solvent in the presence of a base at a temperature from about −15° C. to about 50° C. Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone and 1,3-dibromo-1-propene among others.

Examples of alkyl sulfonates are: allyl-O-tosylate, 3-phenylpropyl-O-trifluoromethane sulfonate and n-butyl-O-methane sulfonate among others.

It is sufficient to use one to four mole equivalents of alkylating agent relative to the erythromycin derivative to be alkylated.

The aprotic solvents described above for the hydroxyl protection are also useful for alkylation.

Examples of the base which can be utilized in the alkylation include potassium hydroxide, cesium hydroxide, tetralkyl ammonium hydroxide, sodium hydride, potassium hydride, potassium isopropoxide, potassium tert-butoxide and potassium isobutoxide among others. The amount of base is usually one to four equivalents relevant to the compound to be alkylated.

Alternatively, the erythromycin derivative can be alkylated with an alkenyl alkylating agent in the presence of a palladium catalyst and a phosphine promoter. Most palladium (0) catalysts will work in this process. Some palladium (II) catalysts, such as palladium (II) acetate, which is converted into a palladium (0) species by in situ reaction with phosphine will work as well. The palladium catalyst can be selected from, but is not limited to, palladium (II) acetate, tetrakis(triphenylphosphine)palladium (0), tris (dibenzylideneacetone) dipalladium, and (tetradibenzylideneacetone) dipalladium, among others. The ratio of the palladium catalyst to the phosphine generally ranges from about 2:1 to 1:8. Suitable phosphines include, but are not limited to, triphenyl phosphine, bis (diphenylphosphine)methane, bis(diphenylphosphine) ethane, bis(diphenylphosphine)propane, 1,4-bis (diphenylphosphine)butane, bis(diphenylphosphine)pentane and tri(o-tolyl)phosphine among others.

The reaction is carried out in an aprotic solvent, preferably at an elevated temperature, preferably at or above 50° C. Useful aprotic solvents include, but are not limited to, N,N-dimethylformamide, dimethylsulfoxide, N-methyl-2-pyrrolidone, hexamethylphosphoric triamide, tetrahydrofuran, 1,2-dimethoxyethane, methyl-t-butyl ether, heptane, acetonitrile, isopropyl acetate and ethyl acetate among others. The most preferred solvents are tetrahydrofuran or toluene.

Useful alkenyl alkylating agents are carbonates and carbamates of allylic hydrocarbons, such as allyl carbonates and allylcarbamates. Presently preferred alkenyl alkylating agents useful have Formula II, shown below,

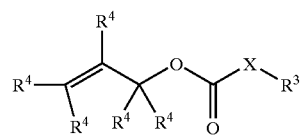

Formula II wherein

X is O or $NR^5$, wherein $R^5$ is alkyl or aryl, or $R^3$ taken together with an $R^4$ may form an aromatic or non-aromatic ring;

$R^4$, at each occurrence, is independently hydrogen, alkyl, halogen, aryl or heteroaryl and $R^3$ is alkyl. Presently preferred alkenyl alkylating agents include those wherein the $R^3$ group is t-butyl, iso-propyl or N, N-diisopropyl. Alkenyl alkylating agents include allyl iso-propyl carbonate, allyl-t-butyl carbonate, allyl N,N-diisopropyl carbamate, 3-(3-quinolyl)-2-propen-1-ol t-butyl carbonate and 1-(3-quinolyl)-2-propene-1-ol t-butyl carbonate. The alkenyl alkylating agents can be obtained by reaction of an alcohol with a wide variety of compounds for incorporating the carbonate or carbamate moiety. The compounds include, but are not limited to, t-butyl chloroformate, 2-(t-butoxycarbonyl-oxyimino)-2-phenylacetonitrile, -t-butoxycarbonyloxy succinimide, di-t-butyl-dicarbonate and 1-(t-butoxy-carbonyl)imidazole, and the reaction is carried out in the presence of an organic or an inorganic base. The temperature of the reaction varies from about −30° C. to about 30° C.

Hydroxamation

An oxime may be prepared from a ketone-containing erythromycin derivative by reaction of that derivative with a hydroxamating agent such as hydroxylamine hydrochloride, in the presence of a base, or hydroxylamine in the presence of an acid as described in U.S. Pat. No. 5,274,085. Useful hydroxamating agents include hydroxylamine hydrochloride or salts thereof; such as the hydrochloride salt or acetate salt. A representative example of the synthetic procedure is as follows. An erythromycin, base, isopropanol, 50% aqueous hydroxylamine (5 to 10 equivalents) and acetic acid (to adjust the pH to less than 7) are combined. The mixture is heated with stirring to 50° C. until the reaction is complete, up to 20 hours. The mixture is then cooled to below 40° C., the pH is adjusted to greater than 9 with aqueous sodium hydroxide, and then the product is extracted into isopropyl acetate, concentrated, filtered and dried.

Aryl Thiomines: Formation and Hydrolysis

Aryl thioimines of the C-9 oxime erythromycin derivatives may be obtained by reaction of the oxime with a trialkyl phosphine and a diaryl disulfide in an organic solvent at a temperature of from about 0° C. to about 30° C. The reaction can be run over a period of from about 15 minutes to about 48 hours. Preferably the reaction is run at 10–20° C. for 2–4 hours. Presently preferred organic solvents include tetrahydrofuran, toluene, pyridine, ethyl acetate and N,N-dimethylformamide. Useful trialkyl phosphines include triethylphosphine, tributylphosphine, trioctylphosphine and tricyclohexylphosphine, among others. A presently preferred aryl disulfide is phenyl disulfide and a presently preferred trialkyl phosphine is tributyl phosphine. The ratio of oxime:phosphine:sulfide may be 1:1–2:1.5–3. Preferably, the ratio of oxime:phosphine:sulfide is 1:1.1:2.

A representative procedure for the hydrolysis of an arylthioimine to an imine is as follows. The imine may be dissolved in THF, and an acid is added, such as concentrated hydrochloric acid, in a sufficient amount to adjust the pH to 2–3. The imine can be isolated as the corresponding hydrochloride salt by filtration, or by extraction into water. The free base can be obtained by pH adjustment with aqueous sodium carbonate and re-extraction into an organic solvent such as ethyl acetate or IPAC.

The procedure for hydrolysis of an aryl thioimine to a ketone is by hydrolysis of the aryl thioimine to an imine, and subsequent hydrolysis of the imine to a ketone, as illustrated in Example 2 which follows. Alternatively, the two steps can be performed in a one-pot procedure, without imine isolation.

The Methods, In General

As set forth in detail herein, it is possible to perform the reactions of the methods of the present invention in a single pot, although it will be appreciated that the described method can be practiced in multiple pots. A "single pot" process is a process that can be performed in a single reaction vessel. It will be appreciated by those of ordinary skill that single pot processes provide certain advantages over multiple pot processes. For example, single pot processes require less handling and/or transfer of components, thereby reducing the risk of accident or mistake. Single pot processes also tend to be less expensive than multiple pot processes as a result of the reduction in handling and transfer of reaction ingredients.

The reactions of the present methods may take place over a wide range of temperatures, for example from 0° C. to 150° C., more preferably from 20° C. to 100° C. The temperature chosen may depend upon various factors. For example, heating may be preferable when the reaction is carried out at a pH value within the range from 4 to 10; on the other hand, the reaction will generally proceed satisfactorily at ambient temperature at a pH of 10 or above.

The time required for the reactions of the methods of the present inventions may vary widely, depending upon many factors, notably the nature of the substrates, the reaction temperature and the pH and nature of the buffer or other medium used, especially the temperature and pH. However, within the preferred ranges indicate above, a period of from 5 minutes to 50 hours will normally suffice.

After completion of the reactions of the methods of the present invention, the desired compound may be recovered from the reaction mixture by conventional means, for example any one or any appropriate combination of the following steps: adjustment of the pH of the reaction mixture; concentration of the reaction mixture, e.g. by evaporating off the solvent under reduced pressure; separating, e.g. by filtration, of the reaction residue; or, if no crystalline precipitate is thereby produced, extracting the mixture with a water-immiscible solvent and then evaporating the solvent from the extract. If desired, the resulting product may be further purified by conventional techniques, for example recrystallization or the various chromatography techniques such as column chromatography or preparative thin layer chromatography.

It is contemplated that other ingredients such as solvents, catalysts, diluents, and other materials may also be present in the reaction mixture if desired, as long as the added extraneous materials do not materially change the nature of the reaction described above, but are added to promote the reaction, suppress side reactions, or improve the purification step of the synthesis.

The compounds which may be prepared by the methods of the present invention include compounds which possess immunosuppressive, anti-microbial, anti-fungal, anti-viral, anti-inflammatory, and anti-proliferative activity, and possess the ability to reverse chemotherapeutic drag resistance. Compounds synthesized by the methods of the present invention would also find utility in the treatment of autoimmune diseases, such as rheumatoid arthritis, Hashimoto's thyroiditis, multiple sclerosis, myasthenia gravis, type I diabetes, uveitis, allergic encephalomyelitis, glomerulonephritis, and the like. Further uses include the treatment and prophylaxis of inflammatory and hyperproliferative skin diseases and cutaneous manifestations of immunologically-medicated illnesses, such as psoriasis, atopical dermatitis, and Epidermolysis bullosa. Further instances where a compound of the invention would be useful include various eye diseases (autoimmune and otherwise) such as ocular pemphigus, Scleritis, and Graves' opthalmopathy, etc.

These Examples are presented to describe preferred embodiments and utilities of the methods of the invention and are not meant to limit the invention unless otherwise stated in the claims appended hereto.

EXAMPLE 1

9-Phenylthioiminoerythromycin-2',4"-dibenzoate was synthesized according to the following procedure.

First, 9-Phenylthioiminoerythromycin was synthesized as follows. Tributylphosphine (5 mL, 20 mmol) was added dropwise to a solution of erythromycin 9-oxime (7.5 g, 10 mmol, obtained by oximating erythromycin A according to the procedure disclosed in U.S. Pat. No. 5,274,085) and diphenyl disulfide (4.4 g, 20 mmol) in tetrahydrofuran (30 mL) at 5–8° C. under a nitrogen atmosphere. After 30 minutes the mixture was quenched by pouring into 5% aqueous solution of sodium carbonate (150 mL). The precipitate was filtered off. Then filter cake was dissolved in a mixture of isopropyl acetate (50 mL) and dichloromethane (50 mL) and dried with magnesium sulfate. The drying agent was filtered off and the solution was concentrated under vacuum. The residue was dissolved in isopropyl acetate (7 ml) and the product was precipitated by the addition of heptanes (70 ml). Filtration and drying gave 4.43 g of phenylthioiminoerythromycin (corresponding to 52% yield).

Then, 9-Phenylthioiminoerythromycin-2',4"-dibenzoate was prepared as follows. 9-Phenylthioiminoerythromycin (1.25 g, 1.5 mmol), benzoic anhydride (1.0 g, 4.4 mmol), triethylamine (0.5 mL, 3.6 mmol) and dimethylaminopyridine (0.18 g, 1.5 mmol) were mixed in tetrahydrofuran (4 mL) for approximately 15 hours at room temperature. The mixture was quenched with water 0.2 ml. After 0.5 hours, it was diluted ethyl acetate (20 mL) and water (20 mL). The organic layer was separated and washed with 10% aqueous sodium carbonate (10 mL). Then the organic layer was concentrated under vacuum and chased with acetonitrile (5 mL). Recrystallization from acetonitrile and drying gave 1.1 g of desired dibenzoate (corresponding to 71% yield). These reactions may also be conducted without isolation of intermediate phenylthioiminoerythromycin.

EXAMPLE 2

Erythromycin A 9-oxime 2',4", -9-tribenzoate was synthesized as follows.

Solid erythromycin A oxime (2.006 kg, 2.677 mol) was charged to a 50-L round-bottom flask (equipped with stir paddle, thermocouple and nitrogen inlet) and dissolved in isopropyl acetate (IPAC, 15.5 kg). The IPAC was concentrated while periodically adding tetrahydrofuran (THF, 45.6 kg), to a final volume of 22 L (K.F.=5.3 mol %). Dimethylaminopyridine (DMAP, 0.3282 kg, 2.67 mol), triethylamine (1.198 kg, 11.84 mol) and benzoic anhydride (2.547 kg, 11.269 mol) were added in one portion to the flask and stirred at 25° C. for 40 hours. The reaction mixture was chilled to 0–5° C. and N,N-dimethylethylenediamine (0.427 kg, 1.5 equiv vs $Bz_2O$ assayed) was added at a rate to maintain an internal temperature of <10° C. (typically ~40 minutes). After the addition was complete, the mixture was stirred for approximately 1 hour at +5° C. until no benzoic anhydride remained. The reaction mixture was transferred to a 100-L vessel, and diluted with methyl-t-butyl ether (MTBE, 20 L). The organic layer was washed with 5% $KH_2PO_4$ solution (2×20 kg). The organic layer was washed with 7% $NaHCO_3$ solution (20 kg), and 27% NaCl solution (10 kg). The organic layer was concentrated in vacuo to remove THF, while periodically charging IPA (16 L), to a final volume of 12 L (NMR showed no THF present). The slurry was warmed to 45° C. with good agitation and stirred for 1.5 hours. The slurry was cooled to −5° C. and stirred for 1.5 hours. The product was filtered and washed with IPA (3×1 L precooled to −10° C.). The tribenzoate was transferred to trays and dried at 50° C. under vacuum with a nitrogen bleed. The yield was 2.323 kg (82%).

The erythromycin A oximetribenzoate was then alkylated with 3-(3-quinolyl)-2-propen-1-ol t-butyl carbonate as follows.

Solid erythromycin A oxime tribenzoate (1000.1 g, 0.942 mol) was charged to a 10-L rotary evaporator flask and dissolved in THF (4.066 kg). The THF was evaporated in vacuo, leaving a foamy oil. The foam was redissolved in THF (3.427 kg) and evaporated again. The resulting material was dissolved in THF (3.500 kg) and transferred to a 12-L round-bottomed flask, equipped with a reflux condenser, nitrogen inlet tube, heating mantle and mechanical stirring apparatus. The vessel was deoxygenated. Solid 3-(3-quinolyl)-2-propen-1-ol, t-butyl carbonate (308.9 g, 1.08 mol, 1.15 equiv) was added in one portion followed by the addition of $Pd_2(dba)_3$ (8.61 g, 0.0094 mol, 0.01 equiv) and dppb (8.02 g, 0.018 mol., 0.02 equiv). The reaction mixture was heated to reflux (65° C.) for approximately 30 minutes until starting material was consumed.

The reaction mixture was chilled to 15° C. Isopropyl alcohol (4.0 L) was added, followed immediately by 2 N NaOH (234 mL, 0.234 mol, 0.5 equiv). Additional sodium hydroxide solution was added as needed to push the hydrolysis to completion. The reaction mixture was poured into MTBE (12 L) and 7% aqueous $NaHCO_3$ (8 L) and agitated 4 minutes. On layer resolution, a black interface formed. The layers were separated, and this interface was removed with the aqueous layer. The organics were washed with 23% aqueous NaCl (8 L) and the layers were separated, again removing any black interface with the aqueous layer. The solvents were removed on the rotary evaporator, with the heating bath at 45° C. The remaining foam was dissolved in THF (4 L) and concentrated by rotary evaporation. The procedure was repeated, leaving the desired product as a dry foam that weighed 1262.1 grams.

EXAMPLE 3

6-O-Propenylquinolinylerythromycin-2',4"-dibenzoate was prepared according to the following synthetic procedure.

First, 9-Imino-6-O-propenylquinolinylerythromycin-2', 4"-dibenzoate was prepared as follows. Tributylphosphine (31 mL, 120 mmol) was added dropwise to a solution of 6-O-propenylquinolinylerythromycin oxime 2',4"-dibenzoate (40 g, 36 mmol, synthesized according to the procedure of Example 2) and diphenyldisulfide (16 g, 73 mmol) in tetrahydrofuran (240 mL) under a nitrogen atmosphere. After 15 hours the mixture was quenched by dropwise addition of conc. HCl (3.5 mL). After 2 hours, the precipitate was filtered off. The filter cake was washed with MTBE (100 mL) and dried to give 33 g of imine as a hydrochloride salt (corresponding to 80% yield).

Then, 6-O-Propenylquinolinylerythromycin-2',4"-dibenzoate was prepared as follows. 9-Imino-6-O-propenylquinolinylerythromycin-2',4"-dibenzoate (2 g, 1.8 mmol) tartaric acid (0.5 g, 3.3 mmol), tetrahydrofuran (8 mL) and water (8 mL) were mixed at room temperature. The mixture was heated to 60–65° C. until not more than 2% of starting material remained by HPLC. The pH of the mixture was adjusted to 7–8 by the addition of aqueous sodium hydroxide (4 N). The aqueous layer was separated; the organic layer was concentrated under vacuum, chased with IPA and slurried in IPA (8 ml). Filtration and drying gave 1.82 g of the ketone (corresponding to 91% yield). These reactions may also be done in a single pot, without imine isolation, to give a 75–80% yield of ketone.

EXAMPLE 4

3-(3-quinolyl)-2-propen-1-ol t-butyl carbonate was prepared as follows. To a 500-mL three-necked round-bottom flask equipped with an overhead mechanical stirrer was charged 3-(3-quinolyl)-2-propen-1-ol (13.03 g, 70.43 mmol) as a mixture of cis and trans isomers (81% cis, and 19% trans), di-t-butyl dicarbonate (16.91 g, 77.48 mmol, 1.11 equiv), tetra n-butyl ammonium hydrogensulfate (742 mg, 2.17 mmol) and methylene chloride (135 mL). The stirred mixture was cooled to 0 to 5° C. at which time aqueous 25% sodium hydroxide (33.3 mL) was added over 45 minutes such that the internal temperature did not rise above 20° C. Upon completion of the reaction (1 to 4 hours), the reaction mixture was diluted with methylene chloride (50 mL) and washed with water (2×125 mL). The organic layer was dried over anhydrous sodium sulfate, filtered, and concentrated in vacuo to provide the 3-(3-quinolyl)-2-propen-1-ol t-butyl carbonate: 18.35 g (91.4%) as an oil. This material can be further purified by chromatography on silica gel to provide purified carbonate as a colorless oil which retains the original ratio of cis and trans isomers: 17.50 g, 87.2%.

EXAMPLE 5

9-Imino-6-O-propenylquinolinylerythromycin-2',4"-dibenzoate was synthesized according to the following procedure.

First, 9-Phenylthioimino-6-O-propenylquinolinylerythromycin -2',4"-dibenzoate was prepared as follows. Propenyl quinoline t-butyl carbonate (PQC, 0.5 g, 1.75 mmol, synthesized according to the procedure of Example 4), 9-phenylthioiminoerythromycin-2',4"-dibenzoate (1.05 g, 1 mmol, obtained by the procedure of Example 1), palladium acetate (5 mg) and bis-(diphenylphosphino)butane (16 mg) were dissolved in tetrahydrofuran (5 mL) under a nitrogen atmosphere. The mixture was heated to reflux. After 3 hours, the mixture was cooled to room temperature and filtered through a layer of FILTROL (0.2 g). The solvent was evaporated, the residue was chased with isopropyl acetate (5 mL) and slurried in isopropyl acetate-heptanes (1:4, 5 mL). Then, solids were filtered off and dried to give 0.9 g of the product (corresponding to 75% yield).

Then, 9-Imino-6-O-propenylquinolinylerythromycin-2',4"-dibenzoate hydrochloride was prepared in the following manner. Hydrochloric acid was added dropwise to a solution of 9-phenylthioimino-6-O-propenylquinolinylerythromycin-2',4"-dibenzoate (0.9 g, 0.7 mmol) in tetrahydrofuran (5 mL) at room temperature until all starting material was consumed. The resulting mixture was diluted with MTBE (5 mL) and filtered. The filter cake was washed with acetonitrile (2 mL) and dried to give 0.74 g of the product (corresponding to 88% yield).

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

I claim:

1. A method for protecting a ketone of a ketone-containing erythromycin derivative as a thioimine comprising the steps of:
   reacting a ketone of a ketone-containing erythromycin derivative with a hydroxamating agent to form an oxime; and then,
   reacting said oxime with a trialkyl phosphine and an aryl disulfide to form an aryl thioimine.

2. The method of claim 1 wherein said ketone is a C-9 ketone, and said aryl thioimine is a C-9 aryl thioimine.

3. The method of claim 1 wherein said trialkyl phosphine is tributyl phosphine.

4. The method of claim 1 wherein said aryl disulfide is diphenyl disulfide.

5. The method of claim 1 wherein said hydroxamating agent is hydroxylamine.

6. The method of claim 1 further comprising deprotecting said aryl thioimine in aqueous acidic solution to form a ketone-containing erythromycin derivative.

7. The method of claim 2 wherein said C-9 ketone containing-erythromycin derivative has a hydroxyl group at C-6.

8. The method of claim 7 wherein said C-9 ketone is protected to alkylate C-6 with an alkylating agent.

9. The method of claim 8 wherein said alkylating agent is an alkenyl alkylating agent.

10. The method of claim 1 wherein said ketone-containing erythromycin derivative is erythromycin A and said aryl thioimine is 9-phenylthioiminerythromycin.

11. The method of claim 1 further comprising hydrolyzing said arylthioimine to an imine with a hydrolyzing agent.

12. A method for deoximating a 6-O-substituted oxime-containing erythromycin derivative comprising the steps of:
   reacting an oxime of a 6-O-substituted oxime-containing erythromycin derivative with a trialkyl phosphine and an aryl disulfide to form an aryl thioimine; and then,
   hydrolyzing said aryl thioimine in aqueous acidic solution to form a ketone- containing 6-O-substituted erythromycin derivative.

13. The method of claim 12 wherein said trialkyl phosphine is tributyl phosphine.

14. The method of claim 12 wherein said aryl disulfide is diphenyl disulfide.

15. The method of claim 12 wherein said 6-O-substituted oxime-containing erythromycin derivative is a C-9 oxime-containing, 2'-hydroxyl-containing, 4"-hydroxyl-containing, C-6-hydroxyl-containing erythromycin derivative.

16. The method of claim 15 further comprising protecting said 2'-hydroxyl and said 4"-hydroxyl of said C-9 oxime-containing, 2'-hydroxyl-containing, 4"-hydroxyl-containing, C-6-hydroxyl-containing erythromycin derivative with at least one hydroxyl-protecting agent to form a 2'- and 4"-hydroxyl protected aryl thioimine after aryl thioimine formation.

17. The method of claim 16 further comprising alkylating said 2'- and 4"-hydroxyl protected aryl thioimine with an alkylating agent to form a 2'- and 4"-hydroxyl protected, C-6-O-alkylated aryl thioimine.

18. The method of claim 17 wherein said 2'- and 4"-hydroxyl protected, C-6-O-alkylated aryl thioimine is 9-phenylthioimino-6-O-propenylquinolinylerythromycin-2',4"-dibenzoate, and said ketone-containing 6-O-substituted erythromycin derivative is 6-O-propenylquinolinylerythromycin-2',4"-dibenzoate.

19. A method of preparing a 6-O-alkyl derivative of a C-9 ketone-containing, C-6 hydroxyl-containing, 2'-hydroxyl-containing, 4"-hydroxyl-containing erythromycin derivative comprising the steps of:
   reacting the C-9 ketone of a C-9 ketone-containing, C-6 hydroxyl-containing, 2'-hydroxyl-containing, 4"-hydroxyl-containing erythromycin derivative with a hydroxamating agent to form a C-9 oxime;
   derivatizing said C-9 oxime with a trialkyl phosphine and an aryl disulfide to form a C-9 aryl thioimine;
   protecting said 2'-hydroxyl and said 4"-hydroxyl of said C-9 aryl thioimine with at least one hydroxyl-protecting agent to form a 2' and 4"-hydroxyl protected C-9 aryl thioimine;
   alkylating said C-6-hydroxyl of said 2' and 4"-hydroxyl protected C-9 aryl thioimine with an alkylating agent to form a C-6-O-alkylated 2' and 4"-hydroxyl protected C-9 aryl thioimine;
   deoximating said 2' and 4"-hydroxyl protected C-6-O-alkylated C-9 aryl thioimine in aqueous acidic solution to form a 2' and 4"-hydroxyl protected C-6-O-alkylated C-9 keto-erythromycin derivative; and then,
   isolating the desired product.

20. The method of claim 19 wherein said trialkyl phosphine is tributyl phosphine.

21. The method of claim 19 wherein said aryl disulfide is diphenyl disulfide.

22. The method of claim 19 wherein at least one hydroxyl-protecting agent is benzoic anhydride.

23. The method of claim 19 wherein said alkylating agent is an alkenyl alkylating agent.

24. The method of claim 23 wherein said alkenyl alkylating agent is propenyl quinoline t-butyl carbonate and a palladium catalyst.

25. The method of claim 19 further comprising deprotecting said 2' and 4"-hydroxyl protected C-6-O-alkylated C-9 keto-erythromycin derivative to form a 2' and 4"-hydroxyl, C-6-O-alkylated C-9 keto-erythromycin derivative.

26. The method of claim 19 wherein said 2' and 4"-hydroxyl protected C-6-O-alkylated C-9 keto-erythromycin derivative is 6-O-propenylquinolinylerythromycin-2',4"-dibenzoate.

27. A method for protecting the ketone of erythromycin A as a thioimine comprising the steps of:
   reacting the ketone of erythromycin A with hydroxylamine to form an oxime; and then,
   reacting said oxime with tributyl phosphine and phenyl disulfide to form 9-phenylthioiminoerythromycin.

28. A method of preparing 6-O-propenylquinolinylerythromycin-2',4"-dibenzoate comprising the steps of:
   reacting the C-9 ketone of erythromycin A with hydroxylamine to form erythromycin oxime;
   derivatizing said oxime with tributyl phosphine and phenyl disulfide to form 9-phenylthioimino erythromycin;
   protecting the 2'-hydroxyl and the 4"-hydroxyl of 9-phenylthioimino erythromycin with benzoic anhydride to form 9-phenylthioimino erythromycin 2',4"-dibenzoate;
   alkylating the C-6-hydroxyl of 9-phenylthioimino erythromycin 2',4"-dibenzoate with propenyl quinoline t-butyl carbonate and a palladium catalyst to form 6-O-propenylquinolinyl-9-phenylthioimino erythromycin 2',4"-dibenzoate;
   converting 6-O-propenylquinolinyl-9-phenylthioimino erythromycin 2',4"-dibenzoate in aqueous HCl into 6-O-propenylquinolinyl erythromycin 2',4"-dibenzoate; and then,
   isolating the desired product.

* * * * *